(12) United States Patent
Wilcken

(10) Patent No.: US 8,525,990 B2
(45) Date of Patent: Sep. 3, 2013

(54) FIBER OPTIC PROBE SCATTEROMETERS FOR SPECTROSCOPY MEASUREMENTS

(75) Inventor: Stephen K. Wilcken, Des Moines, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 13/416,771

(22) Filed: Mar. 9, 2012

(65) Prior Publication Data

US 2012/0170026 A1 Jul. 5, 2012

Related U.S. Application Data

(63) Continuation of application No. 12/372,698, filed on Feb. 17, 2009, now Pat. No. 8,218,142.

(51) Int. Cl.
*G01J 3/28* (2006.01)
(52) U.S. Cl.
USPC .......................................................... 356/326
(58) Field of Classification Search
USPC .................................... 356/51, 338, 326, 328
See application file for complete search history.

(56) References Cited

U.S. PATENT DOCUMENTS

| | | | |
|---|---|---|---|
| 5,004,913 A * | 4/1991 | Kleinerman | 250/227.21 |
| 5,404,218 A | 4/1995 | Nave et al. | |
| 5,625,459 A | 4/1997 | Driver | |
| 6,784,431 B2 | 8/2004 | Shelley et al. | |
| 6,794,631 B2 | 9/2004 | Clark | |
| 6,903,339 B2 | 6/2005 | Shelley et al. | |
| 6,922,241 B2 * | 7/2005 | Kramer | 356/338 |
| 7,113,869 B2 | 9/2006 | Xue | |

* cited by examiner

*Primary Examiner* — Tarifur Chowdhury
*Assistant Examiner* — Abdullahi Nur
(74) *Attorney, Agent, or Firm* — Hanley, Flight & Zimmerman, LLC

(57) ABSTRACT

Fiber optic probe scatterometers for spectroscopy measurements are disclosed. An example device includes an optically transparent illumination tube, an opaque tube, an inner surface of the opaque tube being adjacent an outer surface of the illumination tube and the illumination tube being disposed within the opaque tube, and an optical fiber disposed within and spaced a first distance from the illumination tube, wherein the opaque tube is to be coupled to a spectrometer and an illumination source to provide a light signal along the illumination tube and to collect a scattered light signal via the optical fiber for the spectrometer.

20 Claims, 3 Drawing Sheets

US 8,525,990 B2

FIBER OPTIC PROBE SCATTEROMETERS FOR SPECTROSCOPY MEASUREMENTS

RELATED APPLICATIONS

This patent arises from a continuation of U.S. patent application Ser. No. 12/372,698, filed on Feb. 17, 2009 (now U.S. Pat. No. 8,218,142), the entirety of which is hereby incorporated by reference.

TECHNICAL FIELD

This disclosure generally relates to spectroscopy measurement methods and apparatus including at infrared (IR) wavelengths, and more particularly Fiber Optic Probes for making Non-Destructive spectroscopy measurements including evaluation of the condition of organic containing materials, including fiber reinforced composite materials, such as aircraft structural composite materials.

BACKGROUND

IR spectroscopy measurements may be useful for a variety of purposes including aerospace, automotive and industrial applications, as well as biological and bio-medical applications. For example, infrared (IR) radiation is readily absorbed by organic materials in association with relative motions (vibrations) of atoms such as carbon, hydrogen, oxygen and nitrogen. As such, IR spectroscopy measurements may indicate a condition of a wide variety or organic materials.

For example, organic polymer materials such as resin-fiber composites or adhesives may change over time due to a variety of reasons including heat exposure. Chemical changes to a polymer containing structure may affect the desired properties of the polymer containing structure including structural integrity such as strength of a composite or the adhesive properties of an adhesive.

One problem with prior art approaches to making IR Spectroscopy measurements of polymer containing materials is that a signal-to-noise ratio may be insufficient to determine relative changes in chemistry of the material. For example, prior art Fiber Optic Probes have failed to address the problem of Fresnel reflections from a surface of a sample which may obscure molecular absorption and/or fluorescence spectral data that may be present in the scattered light signal from within a sample.

In addition, prior art devices and methods for making IR Spectroscopy measurements of polymer containing materials have the drawback that they may only be able to measure the outer surface of the material. For example, prior art IR Spectroscopy approaches typically require destruction of a material in an ex-situ setting.

Accordingly, there is a need for an improved spectroscopy non-destructive testing device and method for using the same to non-destructively determine a condition of organic containing materials, including fiber reinforced composite materials, over small sampling areas and/or in hard-to-access configurations with a suitable signal-to-noise ratio.

SUMMARY

In one embodiment, a device for making spectroscopy measurements with reduced or eliminated surface reflections is provided, the device including an elongated member including an outermost opaque thin walled enclosure; an optically transparent thin-walled enclosure adjacent an inner surface of said outermost thin walled enclosure; one or more optical fibers centrally and axially disposed and spaced apart a distance B with respect to the optically transparent thin-walled enclosure; wherein the elongated member is adapted to be coupled to a spectrometer and an illumination source to provide a light signal from the illumination source along said optically transparent thin-walled enclosure and collect a scattered light signal from the sample by said one or more optical fibers to provide to the spectrometer.

In another embodiment, A method of non-destructively determining the condition of an organic containing material sample with reduced or eliminated surface reflections is provided, the method including providing an elongated member including an outermost opaque thin walled enclosure; providing an optically transparent thin-walled enclosure adjacent an inner surface of said outermost thin walled enclosure; providing one or more optical fibers centrally and axially disposed and spaced apart a distance B with respect to the optically transparent thin-walled enclosure; positioning said distal end of said optically transparent thin-walled enclosure adjacent said organic containing material sample; providing an interrogating light signal from an illumination source to said sample along said optically transparent thin-walled enclosure; and collecting a scattered light signal from said sample by said one or more optical fibers and providing said scattered light signal to a spectrometer.

These and other objects, aspects and features of the disclosure will be better understood from a detailed description of the preferred embodiments of the disclosure which are further described below in conjunction with the accompanying Figures.

BRIEF DESCRIPTION OF THE ILLUSTRATIONS

DETAILED DESCRIPTION OF THE PREFERRED EMBODIMENT

The present disclosure achieves the foregoing objects, aspects and features by providing a fiber optic probe scatterometer for accessing small sampling areas and/or hard-to-access or normally inaccessible areas and surfaces for performing non-destructive spectroscopy measurements.

It will be appreciated that the fiber optic probe scatterometer of the present disclosure may be suitably used to non-destructively evaluate any material using any suitable interrogating wavelength of light, but is particularly advantageous for non-destructively evaluating by infrared (IR) spectroscopy, organic containing materials, including fiber reinforced composite materials. The fiber optic probe scatterometer is particularly useful in obtaining spectral data where the sample size desired is on the order of the diameter or width of the fiber optic probe scatterometer, or where the desired sampling surface is accessible through a small opening.

It will further be appreciated that although the fiber optic probe scatterometer of the present disclosure is explained with exemplary use with respect to a carbon fiber-resin composite material, such as a layered carbon composite structure, that the fiber optic probe scatterometer and method of using the same may be equally applicable to the measurement of any organic material having a small sample size and/or accessible through only a small opening, including applications in aerospace, automotive, and industrial fields, as well as biological, medical, and bio-medical fields.

Figure 1:
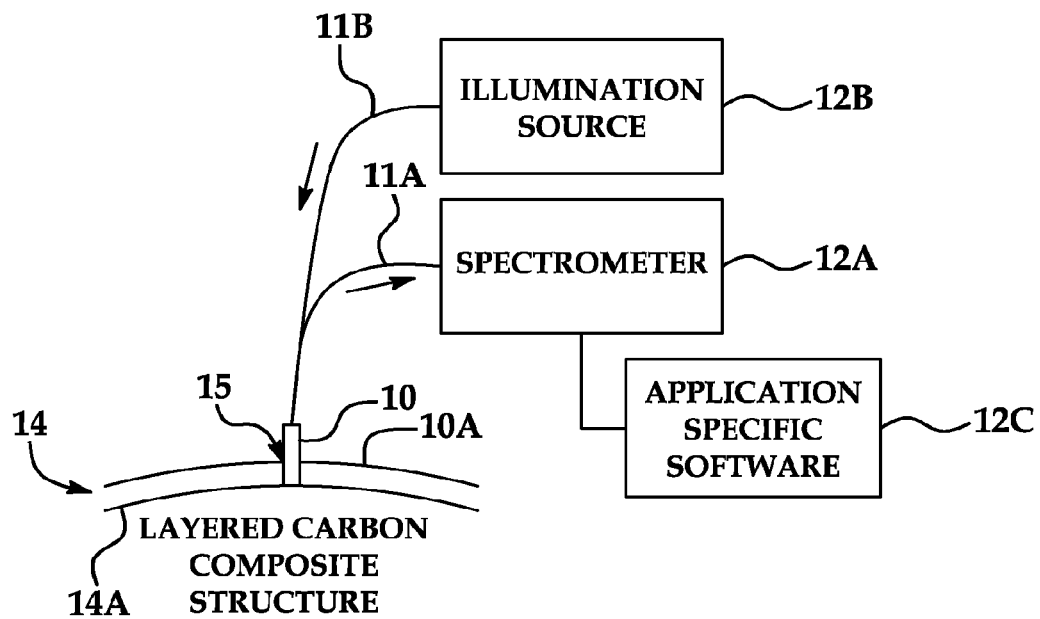
FIG. 1 is a side view of a portion of a fiber optic probe scatterometer assembly in a spectroscopy measurement configuration according to an embodiment.

Referring to FIG. 1 is shown a side view of the fiber optic probe scatterometer assembly according to an embodiment of the disclosure. A fiber optic probe scatterometer 10 may be coupled to one or more fiber optic cables e.g., 11A, 11B, which may in turn be respectively coupled to a spectrometer, e.g., 12A, and an illumination source 12B. The spectrometer 12A may be any spectrometer that may be interfaced with fiber optics, including a hand-held spectrometer. It will be appreciated that the illumination source 12B and the spectrometer 12A may be housed together in a single instrument and that the signal interrogating e.g., 11B and signal collection cable, e.g., 11A may be housed as a single cable including coaxial signal carrying capability.

In one embodiment, the spectrometer 12A may have the ability to make infrared (IR) spectroscopic reflectance measurements including a multi-frequency broadband infrared detection capability including near-IR, midwave-IR, and far-IR wavelengths and the illumination source 12B may have the ability to provide a broadband of interrogating IR wavelengths including near-IR, midwave-IR, and far-IR wavelengths. In one embodiment, the illumination source 12B and the spectrometer 12A may have an ability to make IR spectroscopy measurements over the wavelength region of about 500 to about 4000 nanometers.

In some embodiments, the spectrometer used to make the measurement may use measurement techniques such as reflectance including specular and/or diffuse reflectance. The illumination source 12B may include a multi-frequency infrared source and the spectrometer 12A may include an infrared detector that includes multi-frequency infrared detection capability.

In one embodiment, the diameter of a measuring end (distal end) 10A of the fiber optic probe scatterometer 10, may have a diameter that enables the measuring end 10A to fit through a slightly larger sized hole e.g., 15 within a polymer containing material, such as a fiber (e.g., carbon) reinforced composite structure e.g., 14 in order to access an interior portion such as an interior layer e.g., 14A.

For example, in some embodiments, the fiber optic probe scatterometer measuring end 10A may have a diameter (shown below in FIG. 2 as C) of less than about 2 mm, more preferably less than about 1.5 mm, and even more preferably about 1 mm in diameter or less. It will be appreciated that the 'small opening' through which the measuring end may be inserted may be larger than the measuring end diameter and that the sampled size may be smaller than the measuring end diameter.

Figure 2:
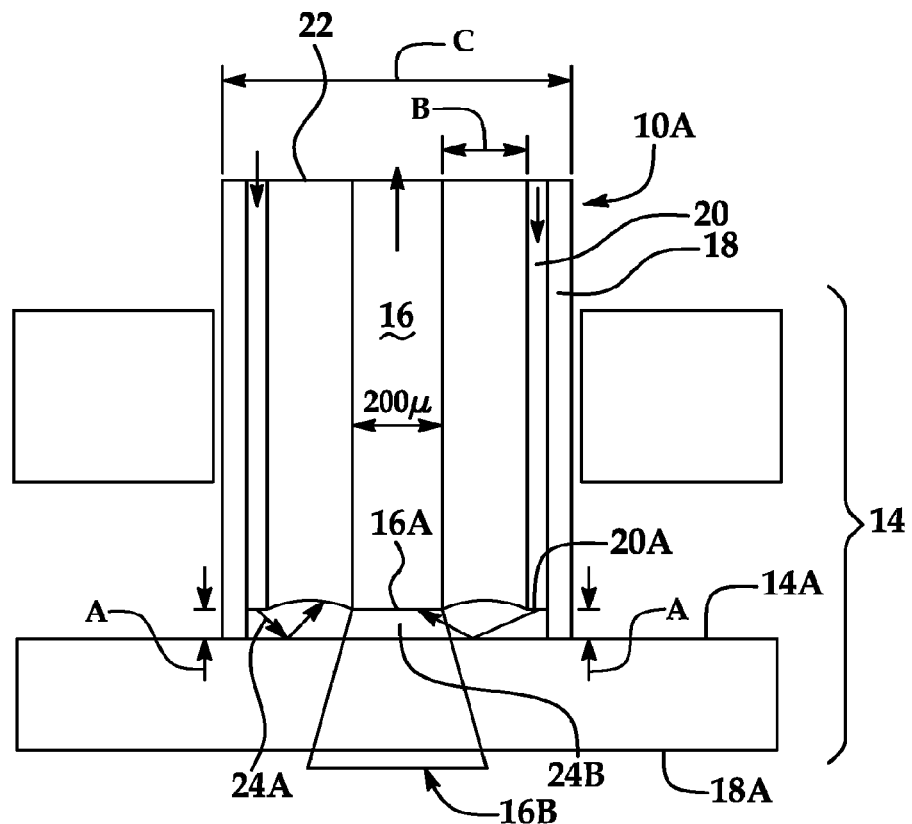
FIG. 2 is a cross sectional view of the measuring end of the fiber optic probe scatterometer according to an embodiment.

Referring to FIG. 2, is shown an enlarged view of a portion of the measuring end 10A of the fiber optic probe scatterometer 10. In some embodiments, the measuring end 10A of the IR fiber optic probe scatterometer may be of different lengths, depending on the application, e.g., the distance required to access a normally inaccessible organic material containing surface (e.g., the surface of interior layer 14A of composite material 14). For example, in some embodiments, the length of the measuring end of the fiber optic probe scatterometer 10A may be from about 1 to about 10 inches in length.

The fiber optic probe scatterometer 10 may include one or more signal receiving optical fibers 16 located axially and centrally (coaxially) with respect to a first outer thin walled tube 18 (jacket) and a second inner concentric thin walled tube 20 (illumination tube). In one embodiment, a single signal receiving optical fiber 16 is provided axially and centrally (coaxially) with respect to the outer tubes 18 and 20 to collect a scattered light signal.

In some embodiments the one or more axially and centrally located optical fibers 16 have a diameter of about 100 microns to about 500 microns, more preferably from about 100 microns to about 300 microns, more preferably from about 150 microns to about 250 microns. As shown, the one or more optical fibers 16 collects a scattered light optical signal from the interior of the probed sample e.g., 14A over a signal collection volume, e.g., 16B while reducing or eliminating collection of sample surface reflections. The one or more optical fibers may be formed of an IR transparent material such as fused silica, preferably low-OH fused silica (dehydroxylated fused silica). Optical fibers which transmit further into the IR, such as silicon fibers and chalcogenide glass fibers, are known in the art. The one or more optical fibers may be coated with a low refractive index cladding as is known in the art.

In one embodiment, an interrogating optical signal from the illumination source e.g., 12B is provided through the second inner concentric thin walled tube 20 (illumination tube). For example, the illumination tube 20 is preferably transparent to the wavelength of interrogating illumination used and may be coated with a low refractive index cladding as is known in the art that allows propagation of light through the illumination tube by total internal reflection. In one embodiment, the illumination tube 20 may be formed of an IR transparent material such as fused silica, preferably low-OH fused silica (dehydroxylated fused silica). In one embodiment the illumination tube 20 may have a wall thickness of from about 10 microns to about 500 microns.

The jacket (outermost) tube 18 may be any structurally stiff and opaque material, and in one embodiment, may be a metal tube, and in another embodiment may be a steel tube, such as a stainless steel tube. Preferably, the illumination tube 20 fits snugly and concentrically within the jacket tube 18. In one embodiment the jacket tube 18 may have a wall thickness of from about thickness of about 10 microns to about 500 microns.

In another embodiment, a structural filler material, e.g., 22 may be included to fill the gap between the one or more optical fibers 16 and the illumination tube 20. The filler material may be an opaque material, such as one or more of a powder metal oxide, glass, or polymer material.

In one embodiment, the one or more optical fibers 16 have a tip (distal end) 16A that is terminated within (axially set back from) a plane defined by the distal ends 18A of the outermost tube 18 which may be co-planar with a sample in contact with the distal ends 18A of the outermost tube 18. In some embodiments, the tip 16A may be axially set back from the distal end of the outermost tube 18A by a distance A, of about 100 to about 500 microns, more preferably from about 200 to about 300 microns, even more preferably about 250 microns. In other embodiments, the tip 16A may be axially set back from the distal end of the outermost tube 18A by between about 1 and about 2 diameters of the one or more optical fibers 16. In another embodiment, the distal end e.g., 20A of the illumination tube 20 and the tip 16A may be axially set back from the distal end of the outermost tube 18A by about the same distance A.

Thus, in one embodiment, the distance A may be selected in order to improve a signal-to-noise ratio by reducing or eliminating surface reflected (Fresnel reflections e.g., specular or diffuse) light from entering the one or more signal collection optical fibers 16. For example, the amount of surface reflected light that undesirably contributes to the signal may be reduced or eliminated by decreasing the setback distance A, e.g., from the tip of one or more optical fibers 16A to a plane that is co-planar with a sample surface. In addition, the setback distance A allows the tip 16A of the one or more optical fibers to be protected from contact with the sample while allowing the distal end 18A of the outermost tube 18 to contact the sample.

In another embodiment, additionally or alternatively to selecting the distance A, a gap distance B, e.g., radial distance B between the inner diameter of the illumination tube 20 and a total outer diameter of the one or more signal collection optical fibers 16 may be selected to improve a signal-to-noise ratio by reducing or eliminating surface reflected light from entering the one or more optical fibers 16. By the term 'total outer diameter' of the one or more optical fibers is meant a minimum outer diameter necessary to enclose the one or more optical fibers. For example, the amount of surface reflected light that undesirably contributes to the signal may be reduced or eliminated by increasing a radial gap distance B.

In operation, the illumination tube may provide a cone of illumination e.g., 24A into the sample e.g., 14A, and the scattered light optical signal from within the sample e.g., 24B may be collected by the one or more signal collection optical fibers 16 which receive the scattered light signal within a conical field of regard e.g., 16B. Thus, by controlling one or more of the distances A and B, as well as the size of the signal collection volume within the sample 16B, the signal to noise ratio may be improved to a level sufficient to allow molecular (chemical) changes within a sample to be more accurately determined. In one embodiment, the size of the signal collection volume 16B may be controlled by selecting the radial gap distance B and the setback distance A such that a width or diameter of the conical field of regard 16B of the signal collection fiber or fibers 16 will intersect with the illumination cone of light projected from the end of the illumination tube 20 only within the interior of the sample, in a definable and controllable manner. Thus, the signal collection field of regard 16B of the signal collection optical fibers 16 may not encompass scattered or reflected light from the upper surface of the sample lying directly under the illumination tube, thereby reducing or eliminating collection of surface reflected light by the one or more optical fibers 16.

It will be appreciated that the distal ends of the outermost tube 18A of the optical scatterometer probe may be placed in contact with a surface of a sample, e.g., 14A to be measured which may serve to provide stability and a repeatable and known distance between the signal collection optical fiber end e.g., 16A and the sample surface, thereby allowing comparison of collected spectra to comparable spectra collected on a sample of a known chemical and/or physical condition (relative calibration spectra).

Referring again to FIG. 1, in exemplary operation, the measuring end 10A of the fiber optic probe scatterometer 10 is inserted into a small opening 15 (e.g., about 1 mm or less) in an external surface of a fiber (e.g., carbon) reinforced composite panel 14 (which may be a structural portion of an aircraft e.g., fuselage or wing), where the hole 15 may be slightly larger than the measuring end 10A of the fiber optic probe scatterometer 10. The tip of the fiber optic probe scatterometer 10, such as the distal ends of the jacket tube 18A, may be in contact or proximate to a surface, to be measured, such as an inner layer of fiber reinforced composite panel 14A. In some embodiments, it will be appreciated that the measurement may be non-destructive and may be made in-situ, e.g., in the field without removing the structural component. It will be appreciated that industry (aircraft) specific requirements may limit the size of the hole or opening that may be permissible in a structural component to not more than (0.040 inches) (e.g., not more than about 1.0 mm).

Referring again to FIG. 2, in operation, an interrogating light signal of a selected band of wavelengths e.g., 24A is provided to the sample surface by the illumination tube, a portion of which propagates into the interior the sample, where it is absorbed and reemitted e.g., 24B into the field of view (within signal collection volume 16B) of a signal collection fiber e.g., 16. As will be appreciated, by reducing or eliminating collection of light reflected from the surface of the sample, the signal strength of re-emitted absorbed light from within the volume of the sample may be improved, thereby allowing more accurate and detailed interrogation of molecular changes occurring within the sample. The absorbed and re-emitted light e.g., 24B is then collected by the one or more signal collection optical fibers e.g., 16 and transferred to the spectrometer 12A for spectral analysis.

In one embodiment, the spectrometer 12A may include appropriate software e.g., 12C either in memory or in storage media accessible by a microprocessor included in or separate from the spectrometer 12A, for comparing the spectral signal of the illumination source and changes imparted by absorption of light by the sample. The software may further include spectral storage capabilities (able to access memory or storage media accessible by a microprocessor included in or separate from the spectrometer 12A) to track relative spectral changes in a sample over time.

In another embodiment, spectroscopic measurements may be made by determining relative differences and/or similarities in measured spectra with respect to spectra from a relative calibration of control samples, such as samples that have been exposed to a known amount and/or type of environmental stress and whose material and/or chemical properties are known, e.g., determined by separate physical property and/or chemical testing.

It will be appreciated that an Absorbance at one or more wavelengths may be calculated according to well known equations based on the intensity of reflected IR light measured, e.g., a diffuse reflectance measurement. It will also be appreciated that depending on the wavelength of the region interrogated, that the absorbance peaks represent complex motions of organic materials including the relative motions (vibrations) of atoms such as carbon, hydrogen, oxygen and nitrogen. Thus, depending on the chemical and/or material property changes associated with spectral changes in a material, a determination as to whether the changes represent acceptable or unacceptable chemical and/or material property changes may be made e.g., by associating a particular absorbance (or reflectance) at one or more wavelengths with a particular acceptable and/or unacceptable absorbance (or reflectance) threshold.

For example, evaluation of the IR spectroscopy measurement may be made in-situ (in the field) automatically by a controller included in or connected to a hand-held or portable IR spectrometer according to a preprogrammed series of steps including providing an indication (e.g., alarm or signal) indicating unacceptable IR spectroscopy measurement values above or below a predetermined threshold. Alternatively, or in addition, the IR spectroscopy measurement results may be stored in memory included in or connected to the IR spectrometer for later analysis.

Figure 3:
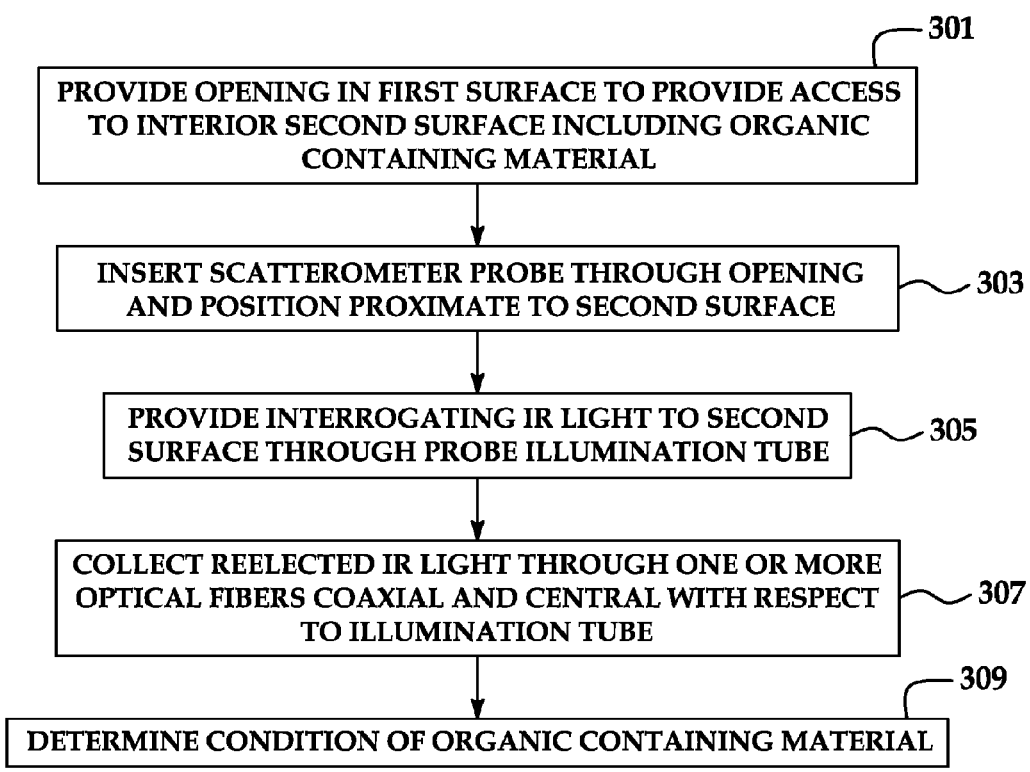
FIG. 3 is a process flow diagram including several embodiments of the disclosure including using the IR fiber optic needle probe.

Referring to FIG. 3 is shown a process flow diagram including several embodiments of the present disclosure. In step 301, an opening suitable for inserting the fiber optic probe scatterometer 10 may be provided in a first surface in order to access a normally inaccessible organic material containing second surface interior with respect to the first surface. In process 303, a measuring end of the fiber optic probe scatterometer may be inserted through the opening and positioned proximate the organic material containing surface. In process 305, the fiber optic probe scatterometer may be coupled to an IR spectrometer and one or more wavelengths of IR light provided through the fiber optic probe scatterometer to the organic material containing surface through a probe illumination tube. In step 307 reflected IR light (spectra) (e.g., with minimal or no surface reflected light) may be collected by one or more optical fibers central and coaxial with respect to the illumination tube and provided to the IR spectrometer. In step 309, a condition of the organic material may be determined based on relative changes in the spectra compared to reference spectra including a known condition of the material.

Figure 4:
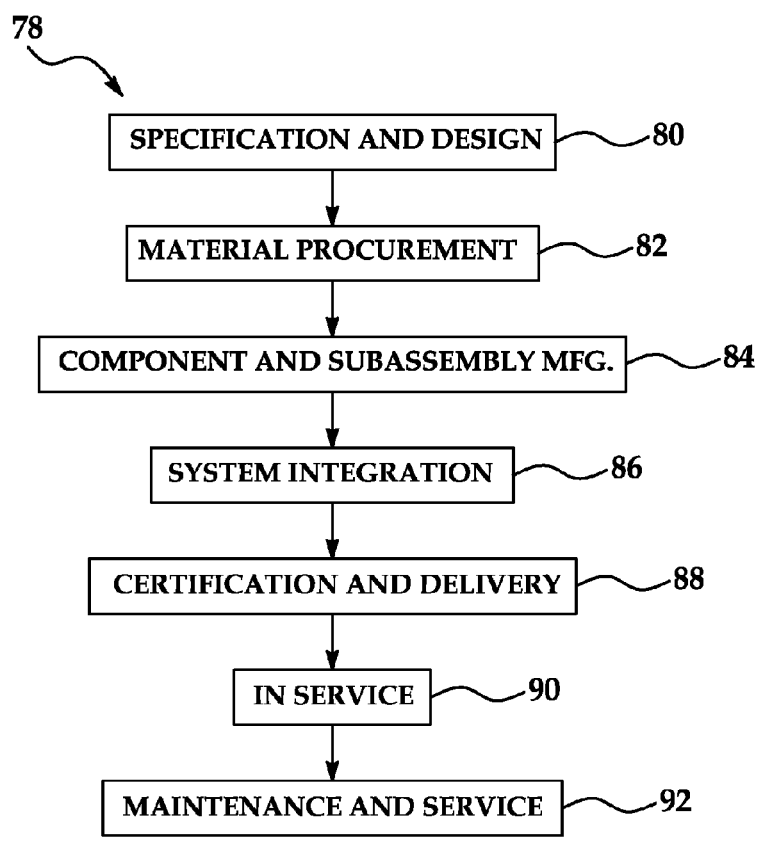
FIG. 4 is a flow diagram of an aircraft and service methodology according to an embodiment.
Figure 5:
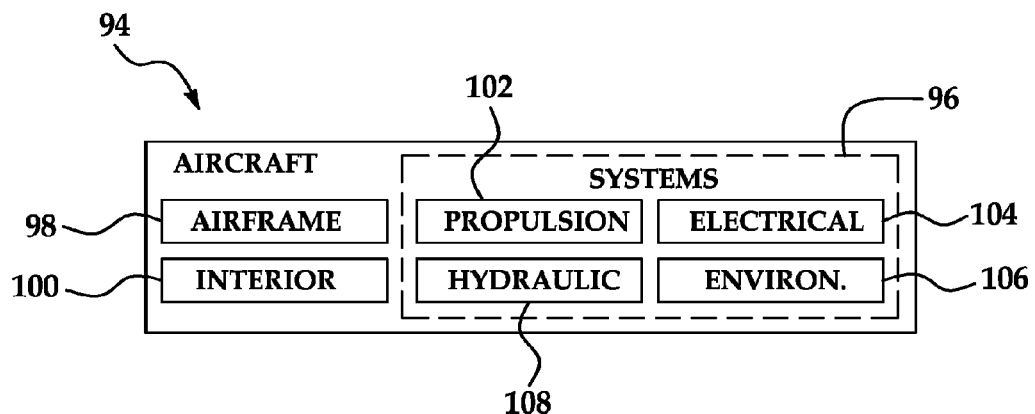
FIG. 5 is a block diagram of an aircraft according to an embodiment.

Referring next to FIGS. 4 and 5, embodiments of the disclosure may be used in the context of an aircraft manufacturing and service method 78 as shown in FIG. 4 and an aircraft 94 as shown in FIG. 5. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 5, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the embodiments may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

While the embodiments illustrated in the Figures and described above are presently preferred, it should be understood that these embodiments are offered by way of example only. The disclosure is not limited to a particular embodiment, but extends to various modifications, combinations, and permutations as will occur to the ordinarily skilled artisan that nevertheless fall within the scope of the appended claims.

What is claimed is:

1. A device, comprising:
    an optically transparent illumination tube to provide a light signal to a sample;
    an opaque tube, an inner surface of the opaque tube being adjacent an outer surface of the illumination tube and the illumination tube being disposed within the opaque tube;
    an optical fiber disposed within and spaced a first distance from the illumination tube, the opaque tube to be coupled to a light detector and an illumination source to provide the light signal to the illumination tube, and the optical fiber to collect a scattered light signal for the light detector when the illumination tube provides the light signal; and
    an opaque layer disposed between the optically transparent illumination tube and the optical fiber.

2. A device as defined in claim 1, wherein the optical fiber is coaxially aligned with the illumination tube and the opaque tube.

3. A device as defined in claim 1, further comprising a gap between the illumination tube and the optical fiber.

4. A device as defined in claim 3, further comprising an opaque material disposed within the gap.

5. A device as defined in claim 1, wherein the opaque tube extends beyond an end of the illumination tube.

6. A device as defined in claim 5, wherein an end of the opaque tube extends beyond an end of the optical fiber.

7. A device as defined in claim 1, further comprising a plurality of optical fibers including the first optical fiber, the plurality of optical fibers disposed within and spaced respective distances from the illumination tube, the plurality of optical fibers to be optically coupled to the light detector to collect the scattered light signal for the light detector.

8. A device as defined in claim 1, wherein the optical fiber has a diameter of from about 150 microns to about 250 microns.

9. A method, comprising:
    providing an interrogating light signal from an illumination source to a material sample via an optically transparent illumination tube, the illumination tube being disposed within an opaque tube such that an inner surface of the opaque tube is adjacent an outer surface of the illumination tube;
    collecting a scattered light signal from the material sample by at least one optical fiber, the at least one optical fiber being disposed within and spaced a first distance from the illumination tube, an opaque layer being disposed between the optical fiber and the illumination tube; and
    providing the scattered light signal to a light detector.

10. A method as defined in claim 9, wherein the opaque tube extends a first distance beyond an end of the illumination tube.

11. A method as defined in claim 10, further comprising selecting the first distance to reduce surface reflected light from entering the at least one optical fiber.

12. A method as defined in claim 9, further comprising:
    providing an opening in a first surface to provide access to a second surface including the material sample; and
    inserting a probe comprising the illumination tube, the opaque tube, and the at least one optical fiber into the opening to a position proximate the second surface.

13. A method as defined in claim 9, wherein the interrogating light signal comprises infrared light.

14. A method of determining a condition of a material sample, comprising:
provide an optically transparent illumination tube to provide a light signal;
providing an opaque tube, an inner surface of the opaque tube being adjacent an outer surface of the illumination tube and the illumination tube being disposed within the opaque tube;
providing an optical fiber disposed within and spaced a first distance from the illumination tube, the opaque tube to be coupled to a light detector and an illumination source to provide the light signal to the illumination tube and the optical fiber to collect a scattered light signal via the optical fiber for the light detector; and
providing an opaque layer disposed between the optically transparent illumination tube and the optical fiber.

15. A method as defined in claim 14, further comprising providing an interrogating light signal from the illumination source to a sample via the optically transparent illumination tube.

16. A method as defined in claim 15, further comprising collecting the scattered light signal from the sample via the optical fiber and providing the scattered light signal to the light detector.

17. A method as defined in claim 14, further comprising providing a gap between the illumination tube and the optical fiber.

18. A method as defined in claim 17, further comprising providing an opaque material within the gap.

19. A method as defined in claim 14, wherein the opaque tube extends a first distance beyond an end of the illumination tube.

20. A method as defined in claim 19, further comprising selecting the first distance to reduce surface reflected light from entering the optical fiber.

* * * * *